United States Patent [19]

Ikeda et al.

[11] Patent Number: 5,639,922
[45] Date of Patent: Jun. 17, 1997

[54] PROCESS FOR TREATMENT OF HYDROPEROXIDE MIXTURE

[75] Inventors: Yoichi Ikeda; Motoo Hazama, both of Toyonaka; Nobuhiro Kawara, Oita; Maki Okumura, Ibaraki; Takanori Ito, Toyonaka, all of Japan

[73] Assignee: Sumitomo Chemical Company, Limited, Osaka, Japan

[21] Appl. No.: 502,537

[22] Filed: Jul. 14, 1995

[30] Foreign Application Priority Data

Jul. 14, 1994 [JP] Japan .................... 6-161976

[51] Int. Cl.$^6$ .................................. C07C 37/08
[52] U.S. Cl. ................ 568/798; 568/799; 568/385; 568/430; 568/814; 568/815
[58] Field of Search .................. 568/385, 430, 568/798, 799, 814, 815

[56] References Cited

U.S. PATENT DOCUMENTS 2,728,797  12/1955  Filar .
5,166,451  11/1992  Takeshita et al. .

FOREIGN PATENT DOCUMENTS

| 0370706 | 5/1990 | European Pat. Off. . |
|---|---|---|
| 51-025011 | 7/1976 | Japan . |
| 51-046094 | 12/1976 | Japan . |
| 52-012183 | 4/1977 | Japan . |
| 59-186958 | 10/1984 | Japan . |
| 60-054357 | 3/1985 | Japan . |
| 62-015074 | 4/1987 | Japan . |
| 62-034755 | 7/1987 | Japan . |
| 63-035558 | 2/1988 | Japan . |
| 2290845 | 11/1990 | Japan . |
| 6056767 | 3/1994 | Japan . |

*Primary Examiner*—Samuel Barts
*Attorney, Agent, or Firm*—Birch, Stewart, Kolasch & Birch, LLP

[57] ABSTRACT

A process is described for the selective decomposition of aromatic primary hydroperoxides by contacting a hydroperoxide mixture containing aromatic primary hydroperoxides and aromatic tertiary hydroperoxides obtained by oxidation of alkylaromatic compounds under non-aqueous conditions with an alkali and an organic aromatic carboxylic acid salt.

20 Claims, No Drawings

PROCESS FOR TREATMENT OF HYDROPEROXIDE MIXTURE

FIELD OF THE INVENTION

The present invention relates to a process for selective decomposition of primary aromatic hydroperoxides in an aromatic hydroperoxide mixture comprising aromatic primary hydroperoxides and aromatic tertiary hydroperoxides used for the production of alkylphenols.

DESCRIPTION OF RELATED ART

A process for selectively decomposing a primary aromatic hydroperoxide by directly treating a hydroperoxide mixture of aromatic primary hydroperoxide and a aromatic tertiary hydroperoxide obtained by liquid phase oxidation in the presence of an alkali with an alkali has been known (JP-B 52-1218). However, the selectivity of this process was not satisfactory.

A process which includes treating the hydroperoxide mixture with an alkali and an organic quaternary ammonium salt, or an organic quaternary ammonium hydroxide, thereby decreasing the primary aromatic hydroperoxide (JP-A 63-35558) has also been known. However, this process was not always satisfactory in that the anion group in the organic quaternary ammonium salt may have a harmful effect on the metal materials of the manufacturing equipment and it was difficult to separate the amine compound which would be formed from the ammonium compound.

Thus, it has been desired to develop a process which readily realizes good selective decomposition of the aromatic primary hydroperoxides in a hydroperoxide mixture on an industrial scale without causing adverse effects to the equipment or the reaction process.

SUMMARY OF THE INVENTION

Therefore, an object of the invention is to provide a process for selective decomposition of aromatic primary hydroperoxides, which comprises contacting a hydroperoxide mixture comprising aromatic primary hydroperoxides and aromatic tertiary hydroperoxides obtained by oxidation of alkylaromatic compounds under non-aqueous conditions with an alkali and an organic aromatic carboxylic acid salt.

It is also an object of the invention to provide a process for producing alkylphenols, which comprises the steps of:

(a) contacting a hydroperoxide mixture comprising aromatic primary hydroperoxides and aromatic tertiary hydroperoxides obtained by oxidation of alkylaromatic compounds under non-aqueous conditions with an alkali and an organic aromatic carboxylic acid salt, and (b) subjecting the reaction mixture obtained in step (a) to a decomposition reaction in the presence of an acid catalyst to obtain alkylphenols.

A further object of the invention is to provide a process for producing alkylphenols, which comprises the steps of:

(a) contacting a hydroperoxide mixture comprising aromatic primary hydroperoxides and aromatic tertiary hydroperoxides obtained by oxidation of alkylaromatic compounds under non-aqueous conditions with an alkali and an organic aromatic carboxylic acid salt, (b) subjecting the reaction mixture obtained in step (a) to a decomposition reaction in the presence of an acid catalyst, and (c) subjecting the reaction mixture obtained in step (b) to hydrogenation in the presence of a catalyst to obtain alkylphenols.

DESCRIPTION OF PREFERRED EMBODIMENTS

According to the present invention, selective decomposition of the primary aromatic hydroperoxides, i.e., high conversion rate for primary aromatic hydroperoxide and high recovery rate for the tertiary aromatic hydroperoxide, can be readily effected on an industrial scale without causing adverse effects to the equipment and the reaction process.

The following will describe the process for selective decomposition of aromatic primary hydroperoxides, which comprises contacting a hydroperoxide mixture comprising aromatic primary hydroperoxides and aromatic tertiary hydroperoxides obtained by oxidation of alkylaromatic compounds under non-aqueous conditions with an alkali and an organic aromatic carboxylic acid salt.

The hydroperoxide mixture comprising aromatic primary hydroperoxides and aromatic tertiary hydroperoxides obtained by oxidation of alkylaromatic compounds under non-aqueous condition is used as the raw material of the present process. For example, alkylaromatic compounds having a methyl group and a secondary alkyl group (e.g. an isopropyl group, a sec-butyl group or cyclohexyl group) as substituents are subjected to oxygenation with oxygen gas or an oxygen-containing gas in non-aqueous condition to give the hydroperoxide mixture. Usually the oxygenation reaction is carried out at a temperature of 30° to 200° C., preferably from 80° to 150° C. and the pressure of oxygen gas or an oxygen-containing gas is in a rang of from 0 to 20 $Kg/cm^2$ as a gauge pressure. An initiator such as azo compound or peroxides (e.g., hydroperoxides of alkylaromatic compounds, benzoyl peroxide) may be added to the reaction system.

The hydroperoxide mixture obtained by the oxygenation can be used after concentrated and is preferably used after neutralization.

The alkylaromatic compounds include, for example, m-cymene, p-cymene, o-cymene, 2,4-dimethylisopropylbenzene, 3,5-dimethylisopropylbenzene, sec-butyltoluene, cyclohexyltoluene, 1-methyl-7-isopropylnaphthalene, sec-butyl-methylnaphthalene, cyclohexyl-methylnaphthalene and the like.

A specific example of the hydroperoxide mixture to be used in the present invention includes, for example, a reaction mixture obtained by oxygenating cymene in non-aqueous condition in liquid phase. The hydroperoxide mixture is preferably further neutralized as mentioned above.

The weight ratio of the aromatic primary hydroperoxides and the aromatic tertiary hydroperoxides in the hydroperoxide mixture is not specially limited and for example, is in a range of from 1:99 to 30:70, preferably, from 2:98 to 25:75.

The aromatic primary hydroperoxides include, for example, compounds of the following formula:

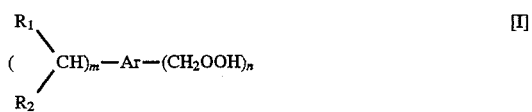

wherein Ar is an aromatic group which may be substituted with a methyl group, $R_1$ and $R_2$ are the same or different and independently represent a lower alkyl group or may be bonded together at their terminals to form with the carbon atom to which they are attached a ring preferably containing 5 or 6 carbon atoms and m and n are independently 1 or 2.

Examples of the aromatic group are benzene and naphthalene.

Examples of the lower alkyl groups for $R_1$ and $R_2$ are $C_1$-$C_4$ alkyl groups such as a methyl group, and ethyl group, a n-propyl group, an isopropyl group and a n-butyl group.

Examples of the ring formed by $R_1$ and $R_2$ are a cyclohexyl group and a cyclopentyl group. Specific examples of the aromatic primary hydroperoxides include, for example, the following compounds.

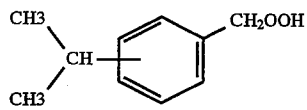

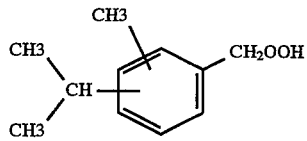

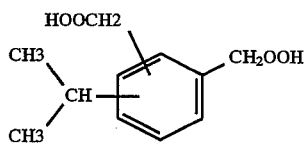

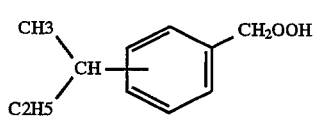

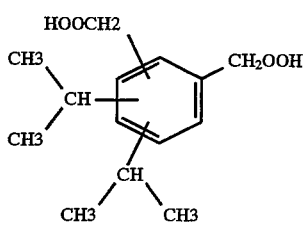

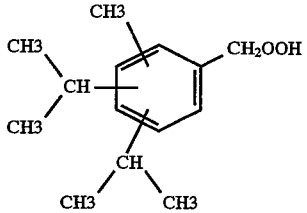

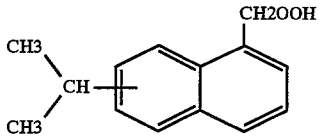

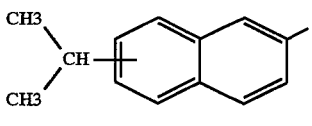

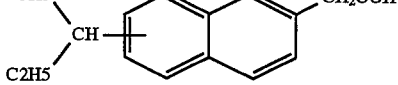

The aromatic tertiary hydroperoxides are not specially limited and include, for example, the compound of the following formula II:

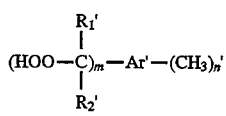

wherein Ar' is an aromatic group which may be substituted with a group of $CHR_1'R_2'$, $R_1'$ and $R_2'$ are independently a lower alkyl group or may be bonded at their terminals to form with the carbon atom to which they are attached a ring preferably containing 5 or 6 carbon atoms, and m' is 1 or 2 and n' is 1 or 2.

Examples of the aromatic group Ar' of the formula I include the same groups mentioned for Ar above.

For $R_1'$ and $R_2'$ the same groups as defined for $R_1$ and $R_2$ can be mentioned.

The aromatic tertiary hydroperoxides include, for example, the following compounds.

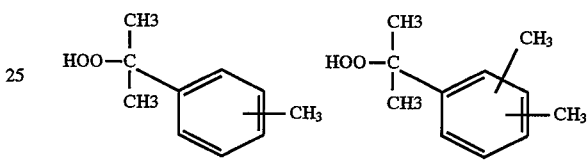

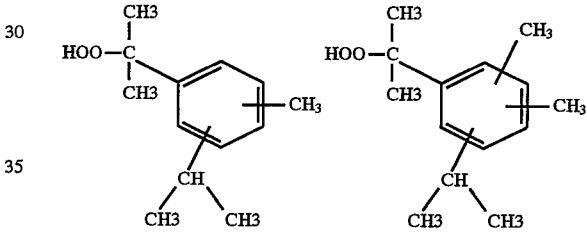

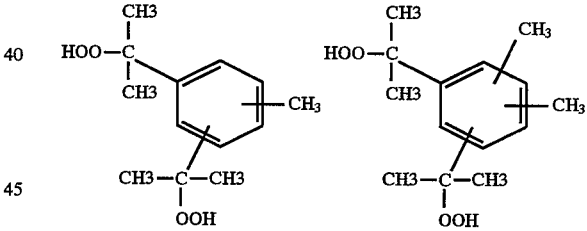

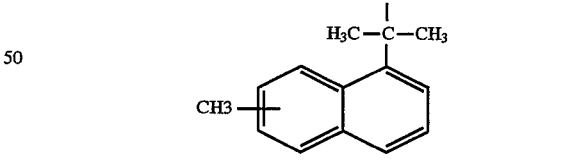

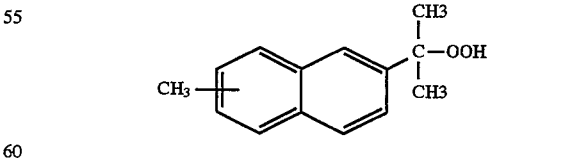

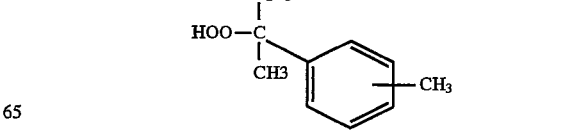

-continued

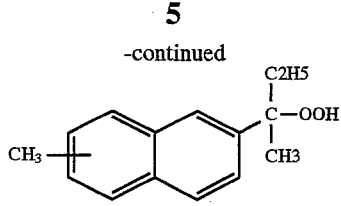

The hydroperoxide mixture may be used after dilution with an organic solvent. The organic solvent to be used includes, for example, hydrocarbons such as benzene, toluene, ethylbenzene, cumene, xylene, cymene, diisopropylbenzene and the like; ketones such as acetone, methyl ethyl ketone, methyl isobutyl ketone and the like.

The amount of the organic solvent to be used is not specially limited, and for example, weight ratio of the organic solvent to the total amount of aromatic hydroperoxide is usually 99:1 to 1:99, preferably in a range of from 95:5 to 70:30.

The organic aromatic carboxylic acid salt to be used in this process is not limited and includes, for example, a compound of the formula III:

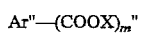

Ar"—(COOX)$_m$"    [III]

wherein Ar" represents an aromatic group, optionally having any substituent, X represents cation, and m" represents an integer of from 1 to 6. The salt can be formed in situ by addition of the free carboxylic acid and the appropriate amount of alkali.

The cation includes metal cations and the like, for example, alkaline metals such as lithium, sodium, potassium and like; alkaline earth metals such as beryllium, magnesium, calcium and the like.

The aromatic group includes, for example, benzene, naphthalene and like which optionally has at least one substituent. The substituent includes, for example, a lower alkyl group which may optionally have a hydroxyl group, acyl group and like.

Specific examples of the organic aromatic carboxylic acid salt of the formula [III] include, for example, sodium benzoate, sodium toluate, sodium ethyl-benzoate, sodium n-propyl-benzoate, sodium isopropyl-benzoate, sodium n-butyl-benzoate, sodium sec-butyl-benzoate, sodium tert-butyl-benzoate, sodium (1-hydroxy-1-methyl)ethyl-benzoate, sodium dimethyl-benzoate, sodium diethyl-benzoate, sodium di-n-propyl-benzoate, sodium di-isopropyl benzoate, sodium di-n-butyl-benzoate, sodium di-sec-butyl-benzoate, sodium di-tert-butyl-benzoate, sodium di(1-hydroxy-1-methyl)ethyl-benzoate, sodium ethyl-methyl-benzoate, sodium methyl-n-propyl-benzoate, sodium methyl-isopropyl-benzoate, sodium n-butyl-methyl-benzoate, sodium sec-butyl-methyl-benzoate, sodium tert-butyl-methyl-benzoate, sodium (1-hydroxy-1-methyl)ethyl-toluate, sodium (1-hydroxy-1-methyl)ethyl-ethyl-benzoate, sodium (1-hydroxy-1-methyl)ethyl-isopropyl-benzoate, sodium (1-hydroxy-1-methyl)ethyl-n-butyl-benzoate, sodium (1-hydroxy-1-methyl) ethyl-sec-butyl-benzoate, sodium (1-hydroxy-1-methyl)ethyl-tert-butyl-benzoate, sodium phthalate, sodium methyl-phthalate, sodium ethyl-phthalate, sodium n-propyl-phthalate, sodium isopropyl-phthalate, sodium n-butyl-phthalate, sodium sec-butyl-phthalate, sodium tert-butyl-phthalate, sodium (1-hydroxy-1-methyl)ethyl-phthalate, sodium (1-hydroxy-1-methyl) ethyl-methyl-phthalate, sodium (1-hydroxy-1-methyl)ethyl-ethyl-phthalate, sodium (1-hydroxy-1-methyl)ethyl-n-propyl-phthalate, sodium (1-hydroxy-1-methyl)ethyl-isopropyl-phthalate, sodium (1-hydroxy-1-methyl)ethyl-n-butyl-phthalate, sodium (1-hydroxy-1-methyl)ethyl-sec-butyl-phthalate, sodium (1-hydroxy-1-methyl)ethyl-tert-butyl-phthalate, sodium benzenetricarboxylate, sodium methyl-benzenetricarboxylate, sodium ethyl-benzenetricarboxylate, sodium n-propyl-benzenetricarboxylate, sodium isopropyl-benzenetricarboxylate, sodium n-butyl-benzenetricarboxylate, sodium sec-butyl-benzenetricarboxylate, sodium tert-butyl-benzenetricarboxylate, sodium benzenetetracarboxylate, sodium hydroxybenzoate, sodium methyl-hydroxy-benzoate, sodium ethyl-hydroxy-benzoate, sodium n-propyl-hydroxy-benzoate, sodium isopropyl-hydroxy-benzoate, sodium n-butyl-hydroxy-benzoate, sodium sec-butyl-hydroxy-benzoate, sodium tert-butyl-hydroxybenzoate, sodium (1-hydroxy-1-methyl)ethyl-hydroxybenzoate, sodium acetylbenzoate, sodium acetyltouate, sodium acetyl-ethylbenzoate, sodium acetyl-n-propylbenzoate, sodium acetyl-isopropylbenzoate, sodium acetyl-n-butylbenzoate, sodium acetyl-sec-butylbenzoate, sodium acetyl-tert-butylbenzoate, sodium acetyl-(1-hydroxy-1-methyl)ethylbenzoate, sodium acetylphthalate, sodium acetyl-benzenetricarboxylate, sodium acetyl-benzenetetracarboxylate, sodium naphthalenecarboxylate, sodium methyl-naphthalenecarboxylate, sodium ethyl-naphthalenecarboxylate, sodium n-propyl-naphthalenecarboxylate, sodium isopropyl-naphthalenecarboxylate, sodium n-butyl-naphthalenecarboxylate, sodium sec-butyl-naphthalenecarboxylate, sodium tert-butyl-naphthalenecarboxylate, sodium acetyl-naphthalenecarboxylate, sodium (1-hydroxy-1-methyl) ethyl-naphthalenecarboxylate, and lithium salts and potassium salts and the like corresponding to these sodium salts, and the position isomers corresponding to them.

Preferably, a specific example thereof is the organic aromatic carboxylic acid salt of the formula [III],wherein Ar" is a benzene ring, which may be optionally substituted, m" is 1 or 2, and X is an alkaline metal cation, more preferable example is the organic aromatic carboxylic acid salt of the formula [III] having 15 or less carbon atoms, wherein Ar" is a benzene ring, which may be optionally substituted, m" is 1 or 2, and X is an alkaline metal cation.

The amount of the organic aromatic carboxylic acid salt to be used is not specially limited and is, for example, in the range of from 0.001 moles to 10 moles, preferably from 0.001 moles to 5 moles, more preferably from 0.1 moles to 5 moles to 1 mole of the aromatic primary hydroperoxides.

The alkali to be used is not limited and includes, for example, alkaline metal hydroxides and alkaline earth metal hydroxides such as sodium hydroxide, potassium hydroxide, lithium hydroxide, calcium hydroxide, barium hydroxide, magnesium hydroxide, strontium and the like. Among them alkaline metal hydroxides are preferably used.

The amount of the alkali is not specially limited, and is, for example, in a range of from 0.1 moles to 20 moles to 1 mole of the aromatic primary hydroperoxides, preferably from 0.5 moles to 10 moles, more preferably from 1 mole to 8 moles for highly selective decomposition of the primary hydroperoxides.

The alkali is usually added to the hydroperoxide mixture as an aqueous alkaline solution.

The ratio of the alkali and water is not specially limited and is, for example, in a range of from 0.5:99.5 to 50:50.

The aqueous alkaline solution may be added if necessary together with a buffer solution prepared from sodium carbonate, sodium bicarbonate, phosphoric acid salt and the like to adjust pH thereof.

The contacting of the hydroperoxide mixture with an alkali and aromatic carboxylic acid salt is usually carried out by stirring. The reaction can be performed either by, for example, a batch, a semi-batch or a continuous method and the like.

The temperature is not specially limited and for example, it is usually in a range of from 50° to 120° C., preferably from 70° to 100° C.

The treatment period is not specially limited and is, for example, in a range of from 0.001 hours to 10 hours, preferably from 0.01 hours to 5 hours.

The process is preferably carried out in an inert atmosphere such as nitrogen atmosphere or the like to avoid a possible further oxidation of the decomposed products such as aromatic aldehydes and arylalkylalcohols.

Completion of the treatment can be readily determined by analyzing the content of the aromatic primary hydroperoxides and the aromatic tertiary hydroperoxides in the reaction mixture by liquid chromatography.

By properly selecting the amount of the organic aromatic carboxylic acid salt, amount of the alkali to be used, the period, the temperature and the like, the decomposition rate of the aromatic primary hydroperxides and the recovery rate of the aromatic tertiary hydroperoxides can be adjusted.

According to the present process, the decomposition rate of the aromatic primary hydroperxides can be set as high as 80% or more or preferably 90% or more, while the recovery rate of the aromatic tertiary hydroperoxides can be maintained as high as 90% or more or 95% or more. To avoid undesirable side reactions of the aromatic primary hydroperoxides in the acid decomposition reaction, the selective decomposition reaction is usually carried out so that the ratio of aromatic primary hydroperoxides to aromatic tertiary hydroperoxides is 1/40 or less, preferably 1/50 or less.

After completion of the reaction, the reaction solution can be supplied to the acid decomposition reaction as it is or after ordinary post-treatment if necessary.

For example, the solution obtained after the reaction process can be separated into an organic layer and an aqueous layer. The hydroperoxide mixture can be readily extracted into the organic layer while an alkali and the organic aromatic carboxylic acid salt can be extracted into the aqueous layer.

The resulting organic layer may be, if necessary, further washed with water or an acidic aqueous solution. The separated aqueous layer can be distilled or can be again used after adjusting the amount of the organic aromatic carboxylic acid salt and the alkali.

Next, a description is made of the process for producing alkylphenols, which comprises the steps of:

(a) contacting a hydroperoxide mixture comprising aromatic primary hydroperoxides and aromatic tertiary hydroperoxides obtained by oxidation of alkylaromatic compounds under non-aqueous conditions with an alkali and an organic aromatic carboxylic acid salt, and (b) subjecting the reaction mixture obtained in step (a) to a decomposition reaction in the presence of an acid catalyst to obtain alkylphenols.

In this process, the reaction mixture obtained in the above-mentioned process (a) is further reacted in step (b).

The following will describe the step of subjecting the reaction mixture obtained in step (a) to a decomposition reaction in the presence of an acid catalyst.

Examples of the acid catalyst to be used are inorganic acids such as sulfuric acid, hydrochloric acid, perchloric acid, $SO_2$, $SO_3$, solid acids (e.g., silica-alumina, alumina), heteropoly acids (e.g., tungstosilicic acid, tungustophosphoric acid, molybdophosphoric acid), organic acids such as benzenesulfonic acid, p-toluenesulfonic acid, cresolsulfonic acid and chloroacetic acid, and acidic ion exchange resin. Preferred acid catalysts are sulfuric acid and cresolsulfonic acid.

The amount of the catalyst to be used is usually in a range of from about 0.0001% to 1% by weight based on the weight of the reaction mixture to be treated.

The reaction temperature is usually in a range of from 30° to 150° C.

In this step, the degree of decomposition of hydroperoxides are checked by liquid chromatography.

After completion of the reaction, the reaction mixture can be used in the subsequent step without undergoing a particular post-treatment, or if necessary, after subjected to a post-treatment such as filtration and neutralization. Alternatively, the reaction mixture can also be used in the subsequent step after removal of acetone produced.

Next, a description is made of the process for producing alkylphenols, which comprises the steps of:

(a) contacting a hydroperoxide mixture comprising aromatic primary hydroperoxides and aromatic tertiary hydroperoxides obtained by oxidation of alkylaromatic compounds under non-aqueous conditions with an alkali and an organic aromatic carboxylic acid salt, (b) subjecting the reaction mixture obtained in step (a) to a decomposition reaction in the presence of an acid catalyst, and (c) subjecting the reaction mixture obtained in step (b) to hydrogenation in the presence of a catalyst to obtain alkylphenols.

The following will describe the step of subjecting the decomposition mixture obtained in the foregoing step to hydrogenation in the presence of a catalyst.

This step can be performed by ordinary catalytic hydrogenation and is attained by introducing hydrogen gas in the reaction system under normal pressure or under pressure, in a range of from 0 to 100 Kg/cm$^2$ as a gauge pressure.

Examples of the catalyst to be used are a metal catalyst such as Pd, Cr, Cu, Pt, Ni, Ru, Rh, Re or a catalyst composed thereof. Preferred are a Pd catalyst or Cu—Cr catalyst. The catalysts can also be used in a supported form on a carrier such as active carbon, titania, zirconia, silica-magnesia, alumina-magnesia, alumina or acidic ion exchange resin. More preferred are Pd/C, Pd/alumina, Pd/TiO$_2$, Cu—Cr/C, Cu—Cr/TiO$_2$, and Pd/acidic ion exchange resin.

The amount of the catalyst to be used is usually in a range of from 0.001% to 20% by weight in terms of metal component, based on the weight of the decomposition mixture to be treated.

In this step, any other catalyst such as acidic catalyst used in the decomposition step may be allowed to coexist. Therefore, the decomposition mixture may be used in this step as it is, without undergoing removal of the catalyst used in the foregoing step.

The reaction temperature is usually in a range of from 0° to 250° C., preferably from 20° to 250° C.

After completion of the reaction, the hydrogenation catalyst can be removed by filtration to give alkylphenols and alkylaromatic compounds such as cymene and acetone, which may be further purified, if necessary, by neutralization and/or distillation.

In the hydrogenation step, certain by-products of the oxygenation reaction and those decomposition products such as aromatic aldehydes (e.g., cumyl aldehydes) and arylalkylalcohols (e.g., cumyl alcohols) produced in the step (a) and olefine compounds such as dimethylstyrene are regenerated as cymene. Therefore, the final yield of the desired products based on the consumed alkylaromatic compounds are increased as compared to prior art methods.

EXAMPLE

The present invention will be further illustrated by way of the following examples, which are not to be construed to limit the scope thereof.

Examples 1 to 3

The reaction was conducted in a four-necked flask equipped with a stick for stirring, a thermometer and a reflux condenser.

20 Parts by weight of an aqueous solution comprising sodium cuminate as an organic aromatic carboxylic acid salt and sodium hydroxide was added to 200 parts by weight of a hydroperoxide mixture comprising primary hydroperoxides of the formula [I] wherein Ar is a benzene ring, $R_1$ and $R_2$ are independently methyl group and m and n are independently 1, and the tertiary hydroperoxides of the formula [II] wherein Ar' is a benzene ring, $R_1'$ and $R_2'$ are independently methyl group, and m' and n' are independently 1. The hydroperoxide mixture used here was obtained by oxygenating cymene in liquid phase under non-aqueous condition and subjected successively to neutralizing and distillation to concentrate the reaction mixture prior to the decomposition reaction. The composition is shown in Table 1. After the resultant solution was reacted with an aqueous alkaline solution with stirring at 90° C. for 1 hour under nitrogen atmosphere, the organic layer was separated from the aqueous layer. The organic layer was analyzed by liquid chromatography.

The compositions of the hydroperoxide mixture, the amounts of the organic aromatic carboxylic acid salt, the amounts of the alkali, the reaction conditions and the analytical results of the organic layer are shown in Table 1.

Comparitive Example 1

The reaction was carried out by the same procedure as Examples 1 to 3, except that sodium cuminate was not used.

The composition of the hydroperoxide mixture, the amount of the alkali, the reaction condition and the analytical result of the organic layer are shown in Table 1.

Example 4

The reaction was performed by the same procedure as Examples 1 to 3, except that the mixture consisting of each sodium salt of cuminic acid, phthalic acid, acetyl benzoic acid, (1-hydroxy-1-methyl)ethylbenzoic acid was used.

The composition of the hydroperoxide mixture, the amount of the organic aromatic carboxylic acid salt, the amount of the alkali, the reaction condition and the analytical result of the organic layer are shown in Table 1.

TABLE 1

| cymene | Hydroperoxide mixture | | |
|---|---|---|---|
| | 1HPO + 3HPO (wt %) | 1HPO/ 3HPO (wt ratio) | (1HPO + 3HPO)/ unreacted (wt ratio) |
| Ex. 1 | 11.7 | 11.4/88.6 | 12.1/87.9 |
| Ex. 2 | 11.7 | 11.4/88.6 | 12.1/87.9 |
| Ex. 3 | 11.7 | 11.4/88.6 | 12.1/87.9 |
| Comparative Ex. 1 | 12.1 | 11.4/88.6 | 12.5/87.9 |
| Ex. 4 | 11.7 | 11.4/88.6 | 12.1/87.9 |

TABLE 1-continued (1HPO: aromatic primary hydroperoxide, 3HPO aromatic tertiary hydroperoxide)

| | Aromatic organic carboxylic acid salt | |
|---|---|---|
| | kind of aromatic organic acid salt | aromatic concentration (wt %) | aromatic organic acid salt 1HPO (molar ratio) |
| Ex. 1 | sodium cuminate | 8.64 | 0.574/1 |
| Ex. 2 | sodium cuminate | 8.85 | 0.590/1 |
| Ex. 3 | sodium cuminate | 4.40 | 0.292/1 |
| Comparative Ex. 1 | — | | 0/1 |
| Ex.4 | sodium cuminate 8.05 + others | | 0.494/1 |

(Others: sodium salt of phthalic acid, acetylbenzoic acid, (1-hydroxy-1-methyl)ethylbenzoic acid, hydroxybenzoic acid and hydroxymethylbenzoic acid: Total concentration of these sodium salt is 5.49 wt %)

| | alkali | | reaction condition | |
|---|---|---|---|---|
| | Concentration (wt %) | NaOH/1HPO (molar ratio) | temp. (°C.) | period (hr) |
| Ex. 1 | 9.40 | 2.91/1 | 90 | 1 |
| Ex. 2 | 7.39 | 2.29/1 | 90 | 1 |
| Ex. 3 | 9.59 | 2.97/1 | 90 | 1 |
| Comparative Ex. 1 | 10.0 | 3.03/1 | 95 | 1 |
| Ex. 4 | 9.82 | 3.04/1 | 90 | 0.5 |

| | analytical result of the organic layer | | |
|---|---|---|---|
| | decomposition rate of 1HPO (%) | recovery ratio of 3HPO (%) | 1HPO/3HPO (molar ratio) |
| Ex. 1 | 99.2 | 96.9 | 1/977 |
| Ex. 2 | 96.5 | 97.2 | 1/213 |
| Ex. 3 | 95.9 | 97.8 | 1/185 |
| Comparative Ex. 1 | 67.6 | 96.3 | 1/23.2 |
| Ex. 4 | 90.1 | 100 | 1/77.9 |

Abbreviations used hereinafter express the following meanings; 3HPO: tertiary hydroperoxide, 1HPO: primary hydroperoxide, CAL: tertiary benzyl alcohol, CUL: primary benzylalcohol, CUA: cumyl aldehyde, CLF: cresol, DMST: dimethylstyrene, IPP: isopropylphenol.

Example 5

900 Parts of Cymene containing 1.13% cymene hydroperoxides as reaction initiator (composition; cymene: 97.79%, 3HPO:1.08%, 1HPO: 0.05%, CAL:0.11%) charged in a reaction vessel equipped with a stirrer, an air-blowing tube, a thermometer and a condenser were reacted at 125° C. under normal pressure with stirring, while air was introduced to the reaction mixture for 8 hours. After completion of the reaction, 920.3 parts (composition; cymene:83.00%, 3HPO:11.39%, 1HPO:2.24%, CAL:0.91%, CUL:0.03%, CUA:0.16%, CLF:0.00%) of the oxidation reaction solution were obtained.

450 Parts of the oxidation reaction solution obtained above were charged in a reaction vessel, to which 45 parts of water were added and then neutralized with 4% sodium hydroxide solution with stirring at 25° C. To the separated oil layer were added 45 parts of an aqueous solution containing 2.7 parts of sodium cuminate and 4.9 parts of sodium hydroxide, and the resulting solution was stirred at 90° C. for an hour under nitrogen atmosphere. Then phase separation gave an organic layer (446 parts, composition; cymene:83.55%, 3HPO:11.00%, 1HPO:0.11%, CAL:1.12%, CUL:0.16%, CUA:1.73%, CLF:0.00%). 1HPO/3HPO was 1/100. Decomposition rate of 1HPO was 95.0% and recovery rate of 3HPO was 95.8%.

433.7 Parts of the reaction oil obtained by the selective decomposition reaction above were concentrated at 70° C./10–20mmHg to recover 348.5 parts of cymene (cymene content: 99.0%) as a distillate and give 83.9 parts of concentrated oil (composition; cymene:20.72%, 3HPO:56.30, 1HPO:0.64%, CAL:5.61%, CUL:0.96%, CUA:8.29%, CLF:0.00%).

49.9 Parts of the concentrated oil obtained above were added dropwise to a refluxing solution of 3.74 parts of acetone and 0.03 part of sulfuric acid with stirring. After the addition, the reaction mixture was kept at 65° C. for 15 min to give 53.2 parts of an acid decomposition reaction solution (composition; cymene:19.44%, 3HPO:0.00%, 1HPO:0.00%, CAL:0.10%, CUL:0.90%, CUA:7.84%, CLF:33.61%, DMST 2.74%). Conversion rate of 3HPO was 100% and a cresol yield based on 3HPO before the acid decomposition reaction was 97.8%.

20.0 Parts of the reaction solution subjected to the acid decomposition reaction, 0.4 part of 5% palladium/titania catalyst and 0.4 part of acidic ion exchange resin (Amberlyst® 15, Rohm & Haas Co., Ltd.) were charged in a stainless steel autoclave reactor and hydrogenated at 45° C. for 2 hours then 75° C. for 1 hour at a hydrogen pressure of 5 Kg/cm$^2$G. After completion of the reaction, catalyst was filtered off. The filtrate was neutralized with aqueous sodium hydroxide solution so that the pH value of the water layer was 7. The reaction mixture was then separated to give 20.0 parts of oil solution (composition; cymene:31.92%, 3HPO:0.00%, 1HPO:0.00%, CAL:0.25%, CUL:0.20%, CUA:0.00%, CLF:33.85%, DMST 0.00%). Cresol yield was 77.5% based on the consumed cymene.

Cresol production process in which the selective decomposition reaction of 1HPO is not conducted.

450 Parts of the oxidation reaction solution obtained in Example 5 were charged in a reaction vessel, to which 45 parts of water were added and then neutralized with 4% sodium hydroxide solution with stirring at 25° C. Then phase separation gave an organic layer (446 parts, composition; cymene:83.55%, 3HPO:11.46%, 1HPO:2.25%, CAL:0.96%, CUL:0.04%, CUA:0.18%, CLF:0.00%). 1HPO/3HPO was 1/5.1. Decomposition rate of 1HPO was 0.5% and recovery rate of 3HPO was 99.8%.

434.5 Parts of the reaction oil obtained by neutralization above were concentrated at 70° C./10–20 mmHg to recover 326.6 parts of cymene (cymene content:99.5%) as a distillate and give 107.4 parts of concentrated oil (composition; cymene:34.00%, 3HPO:44.50%, 1HPO:9.09%, CAL:3.66%, CUL:0.15%, CUA:0.69%, CLF:0.00%).

50.0 Parts of the concentrated oil obtained above were added dropwise to a refluxing solution of 3.74 parts of acetone and 0.03 part of sulfuric acid while stirring. After the addition, the reaction mixture was kept at 65° C. for 15 min to give 53.7 parts of an acid decomposition reaction solution (composition; cymene:31.57%, 3HPO:0.00%, 1HPO:0.00%, CAL:0.00%, CUL:1.47%, CUA:1.42%, CLF:22.67%, DMST:1.01%, IPP:3.48%). Conversion rate of 3HPO was 100% and a cresol yield based on 3HPO before the acid decomposition was 84.74%.

20.0 Parts of the reaction solution subjected to the acid decomposition reaction, 0.4 part of 5% palladium/titania catalyst and 0.4 part of acidic ion exchange resin (Amberlyst® 15, Rohm & Haas Co., Ltd.) were charged in a stainless steel autoclave reactor and hydrogenated at 45° C. for 2 hours then 75° C. for 1 hour at a hydrogen pressure of 5 Kg/cm$^2$G. After completion of the reaction, the catalyst was filtered off. The filtrate was neutralized with aqueous sodium hydroxide solution so that the pH of the water layer was 7. The reaction mixture was then separated to give 20.0 parts of oil solution (composition; cymene:36.30%, 3HPO:0.00%, 1HPO:0.00%, CAL:0.00%, CUL:0.00%, CUA:0.00%, CLF:23.04%, DMST 0.00%, IPP:3.48%). Cresol yield was 59.2% based on the consumed cymene.

We claim:

1. A process for selective decomposition of aromatic primary hydroperoxides, which comprises contacting a hydroperoxide mixture comprising aromatic primary hydroperoxides and aromatic tertiary hydroperoxides obtained by oxidation of alkylaromatic compounds under non-aqueous conditions with an alkali and an organic aromatic carboxylic acid salt.

2. A process according to claim 1, wherein the molar ratio of the organic aromatic carboxylic acid salt to the aromatic primary hydroperoxides is in a range of from 0.001 to 10.

3. A process according to claim 1, wherein the molar ratio of the organic aromatic carboxylic acid salt to the aromatic primary hydroperoxides is in a range of from 0.001 to 5.

4. A process according to claim 1, wherein the molar ratio of the organic aromatic carboxylic acid salt to the aromatic primary hydroperoxides is in the range of from 0.1 to 5.

5. A process according to claim 1, wherein the weight ratio of aromatic primary hydroperoxides and aromatic tertiary hydroperoxides is in the range of from 1:99 to 30:70.

6. A process according to claim 5, wherein the amount of the alkali is in a range of from 0.1 to 20 moles to 1 mole of the aromatic primary hydroperoxides.

7. A process according to claim 6, wherein the amount of the alkali is in a range of from 0.5 to 10 moles to 1 mole of the aromatic primary hydroperoxides.

8. A process according to claim 6, wherein the amount of the alkali is in a range of from 1 to 8 moles to 1 mole of the aromatic primary hydroperoxides.

9. A process according to claim 1, wherein the reaction temperature is 50° to 120° C.

10. A process according to claim 9, wherein the reaction temperature is 70° to 100° C.

11. A process according to claim 1, wherein said alkylaromatic compound is cymene.

12. A process according to claim 2, wherein the weight ratio of aromatic primary hydroperoxides and aromatic tertiary hydroperoxides is in the range of from 1:99 to 30:70.

13. A process according to claim 3, wherein the weight ratio of aromatic primary hydroperoxides and aromatic tertiary hydroperoxides is in the range of from 1:99 to 30:70.

14. A process according to claim 4, wherein the weight ratio of aromatic primary hydroperoxides and aromatic tertiary hydroperoxides is in the range of from 1:99 to 30:70.

15. A process according to claim 1, wherein the aromatic primary hydroperoxide is a compound of formula (I)

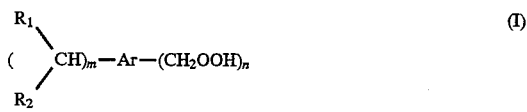

wherein Ar is a benzene or naphthalene group which is unsubstituted or substituted with a methyl group; $R_1$ and $R_2$ are the same or different and independently represent a lower alkyl group or may be bonded together to form a cyclohexyl or cyclopentyl group; and m and n are independent 1 or 2;

the aromatic tertiary hydroperoxide is a compound of formula (II)

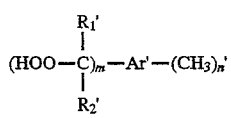

wherein Ar' is a benzene or naphthalene group which is unsubstituted or substituted with a methyl group; $R_1'$ and $R_2'$ are independently a lower alkyl group or may be bonded together to form a cyclohexyl or cyclopentyl group; m' is 1 or 2; and n' is 1 or 2; and the organic aromatic carboxylic acid salt is a compound of formula (III)

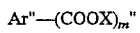

wherein Ar" represents a benzene or naphthalene group which is unsubstituted or substituted with a substituent selected from the group consisting of a lower alkyl group, a lower alkyl group substituted with hydroxyl group and a lower alkyl group substituted with an acyl group; X is a cation selected from alkaline metals and alkaline earth metals; and m" represents an integer of from 1 to 6.

16. A process according to claim 1, wherein the organic aromatic carboxylic acid salt is a compound of formula (III)

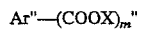

wherein Ar" represents a benzene or naphthalene group which is unsubstituted or substituted with a substituent selected from the group consisting of a lower alkyl group, a lower alkyl group substituted with hydroxyl group and a lower alkyl group substituted with an acyl group; X is a cation selected from alkaline metals and alkaline earth metals; and m" represents an integer of from 1 to 6.

17. A process for producing alkylphenols, which comprises the steps of:

(a) contacting a hydroperoxide mixture comprising aromatic primary hydroperoxides and aromatic tertiary hydroperoxides obtained by oxidation of alkylaromatic compounds under non-aqueous conditions with an alkali and an organic aromatic carboxylic acid salt, and (b) subjecting the reaction mixture obtained in step (a) to a decomposition reaction in the presence of an acid catalyst to obtain alkylphenols.

18. A process according to claim 17, wherein the aromatic primary hydroperoxide is a compound of formula (I)

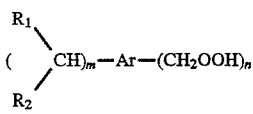

wherein Ar is a benzene or naphthalene group which is unsubstituted or substituted with a methyl group; $R_1$ and $R_2$ are the same or different and independently represent a lower alkyl group or may be bonded together to form a cyclohexyl or cyclopentyl group; and m and n are independent 1 or 2;

the aromatic tertiary hydroperoxide is a compound of formula II

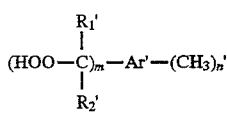

wherein Ar' is a benzene or naphthalene group which is unsubstituted or substituted with a methyl group; $R_1'$ and $R_2'$ are independently a lower alkyl group or may be bonded together to form a cyclohexyl or cyclopentyl group; m' is 1 or 2; and n' is 1 or 2; and the organic aromatic carboxylic acid salt is a compound of formula (III)

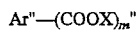

wherein Ar" represents a benzene or naphthalene group which is unsubstituted or substituted with a substituent selected from the group consisting of a lower alkyl group, a lower alkyl group substituted with hydroxyl group and a lower alkyl group substitued with an acyl group; X is a cation selected from alkaline metals and alkaline earth metals; and m" represents an integer of from 1 to 6.

19. A process for producing alkylphenols, which comprises the steps of:

(a) contacting a hydroperoxide mixture comprising aromatic primary hydroperoxides and aromatic tertiary hydroperoxides obtained by oxidation of alkylaromatic compounds under non-aqueous conditions with an alkali and an organic aromatic carboxylic acid salt, (b) subjecting the reaction mixture obtained in step (a) to a decomposition reaction in the presence of an acid catalyst, and (c) subjecting the reaction mixture obtained in step (b) to hydrogenation in the presence of a catalyst to obtain alkylphenols.

20. A process according to claim 19, wherein the aromatic primary hydroperoxide is a compound of formula (I)

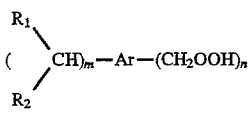

wherein Ar is a benzene or naphthalene group which is unsubstituted or substituted with a methyl group; $R_1$ and $R_2$ are the same or different and independently represent a lower alkyl group or may be bonded together to form a cyclohexyl or cyclopentyl group; and m and n are independent 1 or 2;

the aromatic tertiary hydroperoxide is a compound of formula II

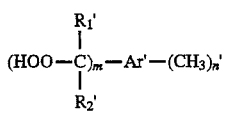

wherein Ar' is a benzene or naphthalene group which is unsubstituted or substituted with a methyl group; $R_1'$ and $R_2'$ are independently a lower alkyl group or may be bonded together to form a cyclohexyl or cyclopentyl group; m' is 1 or 2; and n' is 1 or 2; and the organic aromatic carboxylic acid salt is a compound of formula (III)

wherein Ar" represents a benzene or naphthalene group which is unsubstituted or substituted with a substituent selected from the group consisting of a lower alkyl group, a lower alkyl group substituted with hydroxyl group and a lower alkyl group substituted with an acyl group; X is a cation selected from alkaline metals and alkaline earth metals; and m" represents an integer of from 1 to 6.

* * * * *